(12) United States Patent
Scott et al.

(10) Patent No.: US 6,288,292 B1
(45) Date of Patent: *Sep. 11, 2001

(54) PROCESS AND APPARATUS FOR VAPORIZATION OF HALOCARBONS

(75) Inventors: John David Scott, Near Northwich; Charles Brian Blake, Guilden Sutton; Paul Nicholas Ewing, Warrington; Jeremy Charles Bauser Hunns, Northwich, all of (GB)

(73) Assignee: Imperial Chemical Industries, PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/449,598

(22) Filed: Nov. 29, 1999

Related U.S. Application Data

(63) Continuation of application No. 08/533,590, filed on Sep. 25, 1995, now Pat. No. 6,034,288, which is a continuation of application No. PCT/GB94/00784, filed on Apr. 14, 1994.

(51) Int. Cl.[7] ................................................. C07C 17/08
(52) U.S. Cl. .................................................. 570/164
(58) Field of Search .................................... 570/164, 102, 570/121, 161

(56) References Cited

U.S. PATENT DOCUMENTS

| 3,969,449 | 7/1976 | Shires et al. . |
| 5,051,537 | 9/1991 | Manzer . |
| 6,034,288 | * 3/2000 | Scott et al. ........................ 570/102 |

FOREIGN PATENT DOCUMENTS

| 0 408 005 B1 | 1/1991 | (EP) . |
| 0 537 759 A2 | 4/1993 | (EP) . |
| WO 91/04955 | 4/1991 | (WO) . |

* cited by examiner

*Primary Examiner*—Alan Siegel
(74) *Attorney, Agent, or Firm*—Cook, Alex, McFarron, Manzo, Cummings & Mehler Ltd.

(57) ABSTRACT

Prior to carrying out a gaseous phase chemical reaction, a liquid phase organic compound which is prone to degrade is vaporised at elevated pressures with the aid of a second compound. In one embodiment of the invention vaporisation is effected by co-vaporising a mixture of the two compounds in a vaporiser. In another embodiment, the first compound is injected into a hot gaseous stream and undergoes atomisation into droplets which then vaporise within the gaseous stream. The second compound is used to assist the atomisation process and/or to sweep atomised droplets of the first compound away from hot surfaces where the first compound would otherwise tend to undergo degradation if the droplets are allowed to reside in contact with such surfaces.

13 Claims, 4 Drawing Sheets

PROCESS AND APPARATUS FOR VAPORIZATION OF HALOCARBONS

This is a continuation under 35 U.S.C. Section 120 of U.S. Ser. No. 08/533,590 filed on Sep. 25, 1995 now U.S. Pat. No. 6,034,288, which is a continuation of International Application PCT/GB94/00784 filed on Apr. 14, 1994 and which designated the U.S.

The present invention relates to chemical processes involving the vaporisation of a liquid phase organic compound which is to undergo chemical reaction in the course of the process. The invention has particular application to organic compounds which can be vaporised satisfactorily at atmospheric pressure but become prone to degradation when vaporisation is effected at elevated pressure, with consequent elevation of the boiling point (or bubble point) of the compound.

For instance, when trichloroethylene is vaporised at elevated pressures such that the boiling point thereof is in excess of 150° C., degradation products are formed which cause fouling of heat exchange surfaces thereby impairing performance (vaporisation efficiency). Also, such degradation of trichloroethylene leads to the formation of undersirable chemical species which are vaporised and pass into the process utilising the vaporised trichloroethylene.

Trichloroethylene is used in the production of compounds such as 1,1,1,2-tetrafluorethane by reaction thereof with a stoichiometric excess of HF in the presence of a fluorination catalyst. Where this process is carried out at elevated pressure (which is advantageous since the plant for carrying out the process can be made compact), problems arise in achieving satisfactory vaporisation of the trichloroethylene.

According to a first aspect of the invention there is provided a process for carrying out a chemical reaction involving a first organic compound which has been vaporised from the liquid phase under conditions which render the liquid phase form of the pure compound prone to degrade, characterised in that vaporisation of said first compound from the liquid phase is effected using a second compound in such a way as to suppress degradation of said first compound.

The chemical reaction may be one involving both compounds as reactants as in, for example, the fluorination of trichloroethylene using hydrogen fluoride. However, we do not exclude the possibility of the chemical reaction being one which does not involve the second compound as a reactant (primary or otherwise), eg the chemical reaction may be one involving the isomerisation of a vaporised chlorocarbon in the presence of an isomerisation catalyst, eg the isomerisation of HCFC 123a to produce HCFC 123.

The invention in all aspects thereof defined herein has particular application to the vaporisation of halocarbons (which term is used herein to include halogenated compounds which incorporate hydrogen) and more specifically chlorocarbons such as chloroethenes, eg trichloroethylene and perchloroethylene, and chloroethanes such as 1,1,1,2-tetrachloroethane and 1,1,2,2-tetrachloroethane.

The term "degradation product" as used herein is to be construed as including within its ambit, derivatives of said organic compound which are not desired in the context of the particular chemical reaction. For instance, in the case of 1,1,2,2-tetrachloroethane, the chemical reaction may be one in which it is to be converted to 1,1,2-trichloro-2-fluoroethane but may be prone to convert to trichloroethylene if subjected to high temperature whilst in the liquid phase (eg as a result of coming into contact with a hot metal surface) and, in this instance, for the purposes of the present invention, trichloroethylene may be regarded as a degradation product of 1,1,2,2-tetrachloroethane.

When used in suppressing degradation of said first compound, the second compound may be in the liquid or gas phase. In the former case, the degradation suppression may be effected by co-vaporising the first compound in admixture with the second compound.

According to a second aspect of the present invention there is provided a process for carrying out a chemical reaction at elevated pressure, comprising vaporising under elevated pressure conditions a liquid phase organic compound which forms one of the reactants and is prone to degrade when vaporised under such conditions, and reacting the vaporised compound with at least one other reactant in the gaseous phase under conditions which permit the reaction to proceed, characterised by modifying the boiling characteristics of the organic compound such that vaporisation can be effected at reduced temperature thereby preventing or substantially reducing the production of degradation products.

Preferably the boiling characteristics of the organic compound are modified by co-vaporising the compound in admixture with another compound which may form one of the reactants. The compound which is added to said organic compound is preferably one which provides a mixture capable of forming a minimum boiling azeotrope. In general, the second compound will have a boiling point lower than that of the first compound.

According to another aspect of the present invention there is provided a process for effecting fluorination of a chlorocarbon compound at elevated pressure, comprising vaporising the compound under elevated pressure conditions at which the boiling point of the compound per se is such that vaporisation of the compound per se is accompanied by degradation of the compound if vaporised at that boiling point, and reacting the vaporised compound with a fluorinating agent in the gaseous phase under conditions with permit the reaction to proceed, characterised by the selection of hydrogen fluoride as the fluorinating agent and effecting vaporisation of the chlorocarbon by co-vaporising a mixture of the chlorocarbon compound with hydrogen fluoride whereby the boiling temperature of the chlorocarbon compound/HF mixture is such that vaporisation thereof is accompanied by substantially less degradation of the chlorocarbon compound.

Preferably the chlorocarbon compound is a chloroethene such as trichloroethylene or perchloroethylene, or a chloroethane such as 1,1,1,2-tetrachloroethane or 1,1,2,2-tetrachloroethane.

In yet another aspect of the invention there is provided a process for carrying out a chemical reaction involving a halocarbon in its vapour phase, in which prior to the reaction the halocarbon is vaporised under elevated pressure conditions at which the boiling point of the compound per se is such that vaporisation of the compound per se is accompanied by degradation of the compound if vaporised at that boiling point, characterised in that the halocarbon is co-vaporised in admixture with hydrogen fluoride whereby the boiling temperature of the halocarbon compound/HF mixture is such that vaporisation is accompanied by substantially less degradation of the halocarbon compound.

Typically the reduction in degradation is at least 50% by weight, ie the amount of degradation products produced is at least 50% by weight less than would occur if the pure halocarbon is vaporised at its boiling point under said elevated pressure conditions.

In one embodiment of the chemical reaction may comprise isomerisation of the halocarbon compound, eg the isomerisation of 1,2-dichloro-1,2,2-trifluoroethane (HCFC 123a) in its vapour phase to the more stable 1,1-dichloro-2,2,2-trifluoroethane (HCFC 123).

In another embodiment of the invention the chemical reaction may comprise the fluorination of a chlorocarbon such as a chloroethane or a chloroethene in which case vaporisation of the chlorocarbon by co-vaporisation with HF and the HF may also constitute the fluorinating agent. For example, the chloroethene may comprise trichloroethylene and the reaction is one involving fluorination of trichloroethylene. We have found that, whilst vaporisation of trichloroethylene at elevated pressure would normally result in the production of degradation products, co-vaporisation of the chloroethylene in admixture with HF has a marked affect on the boiling point to the extent that even small additions of HF allow efficient vaporisation of the chloroethylene under elevated pressure conditions without any significant degradation of the chloroethylene.

Where the chloroethene comprises trichloroethylene, the elevated pressure at which fluorination is carried out is typically in excess of that at which the boiling point of trichloroethylene is 150° C., more preferably 180° C. Usually the trichloroethylene will be vaporised at a temperature somewhat below that of the process stream into which it is introduced with the advantage that the trichloroethylene so introduced has a cooling affect on the process stream.

Certain aspects of the invention as defined above are primarily concerned with effecting vaporisation of a liquid phase organic compound so that the resulting vapour can then be fed as such to a process utilising the vapourised form of the compound. The following aspects of the invention are concerned with processes in which the organic compound is fed in its liquid phase form to the process in which it is to be utilised, in circumstances where the compound is to be vaporised by contact with a hot gaseous stream in the proximity of hot surfaces such that, if liquid phase droplets of the compound are allowed to reside in contact with such surfaces, the compound is prone to degrade.

In particular, the following aspects of the invention concern a chemical process involving contact between a hot gaseous stream and an organic compound which, when in the liquid phase, is prone to degrade if allowed to reside in contact with a hot surface, said method comprising injecting said organic compound in its liquid phase into a conduit through which the hot gaseous stream flows in such a way that the liquid atomises and vaporising the liquid droplets so formed by contact with the hot gaseous stream.

The gaseous stream and/or a gaseous compound present in the gaseous stream can be utilised to prevent the degradation of organic compound as a result of contact of said organic compound in its liquid, phase with surfaces heated by said gaseous stream.

Such utilisation of the gaseous stream and/or said gaseous compound may take various forms.

In accordance with one feature of the invention the organic compound is injected as a liquid phase stream together with a second compound as a gas phase stream into a conduit through which the hot gaseous stream flows so that the first organic compound is atomised at least in part by interaction between the injected streams, the liquid droplets so formed being vaporised by contact with the hot gaseous stream.

Thus, the atomisation of the liquid phase organic compound may be effected at least in part by the interaction between the injected streams. The interaction between the hot gaseous stream and the injected liquid phase stream may also serve to effect atomisation.

This feature finds application for instance in circumstances in which the throughput of the hot gaseous stream may vary for example between a full load condition and a turn-down condition where the throughput is substantially reduced, eg 75% or less, and often 50% or less, than the throughput under full load. In such a case, the throughput in turn-down conditions may be insufficient to secure efficient atomisation of the injected liquid phase stream by the hot gaseous stream. The interaction between the injected streams may therefore be used to compensate for loss of efficiency in atomisation in turn-down conditions.

The second compound, injected as a gas phase stream, is preferably one of the components forming the process gas stream. For example, in fluorination processes, the injected gas phase stream may comprise hydrogen fluoride.

In another feature of the invention, the hot gaseous stream and/or gaseous phase compound may be controlled in such a way as to either substantially eliminate contact between heated surfaces and the droplets or at least reduce the residence time of contact between said heated surfaces and the droplets to such an extent that vaporisation of the liquid occurs before any significant degradation can develop.

This may be implemented for instance by injecting said organic compound as a liquid phase stream into a conduit through which the hot gaseous stream flows, the first organic compound being atomised at least in part by interaction with the hot gaseous stream and the droplets so formed being vaporised by contact with the hot gaseous stream; and injecting a second compound as a gas phase stream into the conduit downstream of the location of injection of the first compound to compensate for the pressure drop in the wake of the injected stream of said first compound and thereby prevent deposition of said liquid droplets on the conduit wall immediately downstream of the location of injection of the first compound.

In a further development the reduction in residence time may be implemented by controlling the gaseous stream and/or said gaseous compound so as to "sweep" the heated surfaces and thereby clear any droplets settling thereon and resuspend them in the gaseous stream.

Thus in accordance with this development of the invention there is provided a chemical process involving contact between a hot gaseous stream and an organic compound which, when in the liquid phase, is prone to degrade if allowed to reside in contact with a hot surface at or above a predetermined temperature, said process comprising:

atomising the organic compound by injection thereof into a conduit through which the hot gaseous stream flows, the conduit wall or walls being heated at least in part by the hot gaseous stream to at least said predetermined temperature;

vaporising the liquid droplets so formed by contact with the hot gaseous stream as the liquid droplets are transported by the hot gaseous stream downstream of the location of injection; and introducing a gas phase component into the conduit at a location downstream of the location of injection of the organic compound so as to to form a boundary layer at the conduit wall or walls for reducing or preventing deposition of the liquid droplets on the conduit wall or walls.

The gaseous component used to develop the boundary layer may be constituted by part of the hot gaseous stream diverted from the main flow and re-introduced into the conduit at said downstream location. Alternatively or additionally the gaseous component may comprise an auxiliary gas which itself may participate in a subsequent chemical reaction with the organic compound; for instance where the chemical reaction is one involving fluorination of a halocarbon, the auxiliary gas may comprise HF.

In accordance with another aspect of the invention there is provided a liquid injection device for the introduction of liquid phase organic compounds into a process gas stream, comprising:

a conduit section for coupling into, or forming part of, a conduit for the process gas stream;

a Venturi arrangement housed within the conduit section and including a throat section and a diffuser section downstream of the throat section;

means for partitioning the process gas flow into a first stream which passes through the Venturi arrangement and a second stream which by-passes at least part of the Venturi arrangement;

a plurality of nozzles for injecting the liquid phase compound into the Venturi arrangement at, or in close proximity to, the throat section whereby the liquid is atomised to produce droplets which are vaporised by the process gas stream; and means for introducing the second stream into the Venturi arrangement at a location downstream of the nozzles in such a way as to create a moving layer of gas over the surfaces of the Venturi arrangement whereby unvaporised liquid droplets migrating towards such surfaces are prevented from residing in contact therewith.

Other aspects and features of the invention will become apparent from the following description of specific embodiments of the invention and also the appended claims.

The various aspects of the invention will now be described by way of example only with reference to the accompanying drawings, in which.

Figure 1:
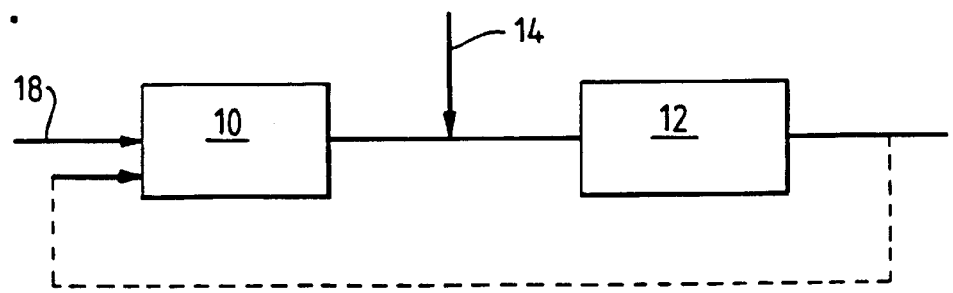
FIG. 1 is a schematic view illustrating the production of 1,1,1,2-tetrafluoroethane in a two-stage process as described in our prior EP-A-449617, the entire contents of which are incorporated herein by reference.

Referring to FIG. 1, a process for the production of 1,1,1,2-tetrafluoroethane (134a) is carried out in a first reactor 10 in which the vapour phase fluorination of 1,1,1-trifluoro-2-chlorethane (133a) with hydrogen fluoride is effected in the presence of a fluorination catalyst to form a product containing 134a, hydrogen chloride and unreacted starting materials, and a second reactor 12 to which the gaseous stream derived from reactor 10 is fed along with vaporised trichloroethylene introduced via line 14, the resulting vapour phase reaction in reactor 12 taking place in the presence of a fluorination catalyst and resulting in a product containing 133a, 134a, hydrogen chloride and trichloroethylene. The product from reactor 12 is treated to separate 134a and hydrogen chloride from 133a, unreacted hydrogen fluoride and trichloroethylene and the latter fraction comprising 133a, unreacted hydrogen fluoride and trichloroethylene is recycled via line 16 to the first reactor 10 to which additional hydrogen fluoride is supplied via line 18. The reaction in reactor 12 is typically carried out at a temperature lower than the temperature of the gas stream exiting the reactor 10 and consequently it is necessary to cool the gas stream at some point along line 14 and line 14 may therefore include a cooler for this purpose.

Figure 2:
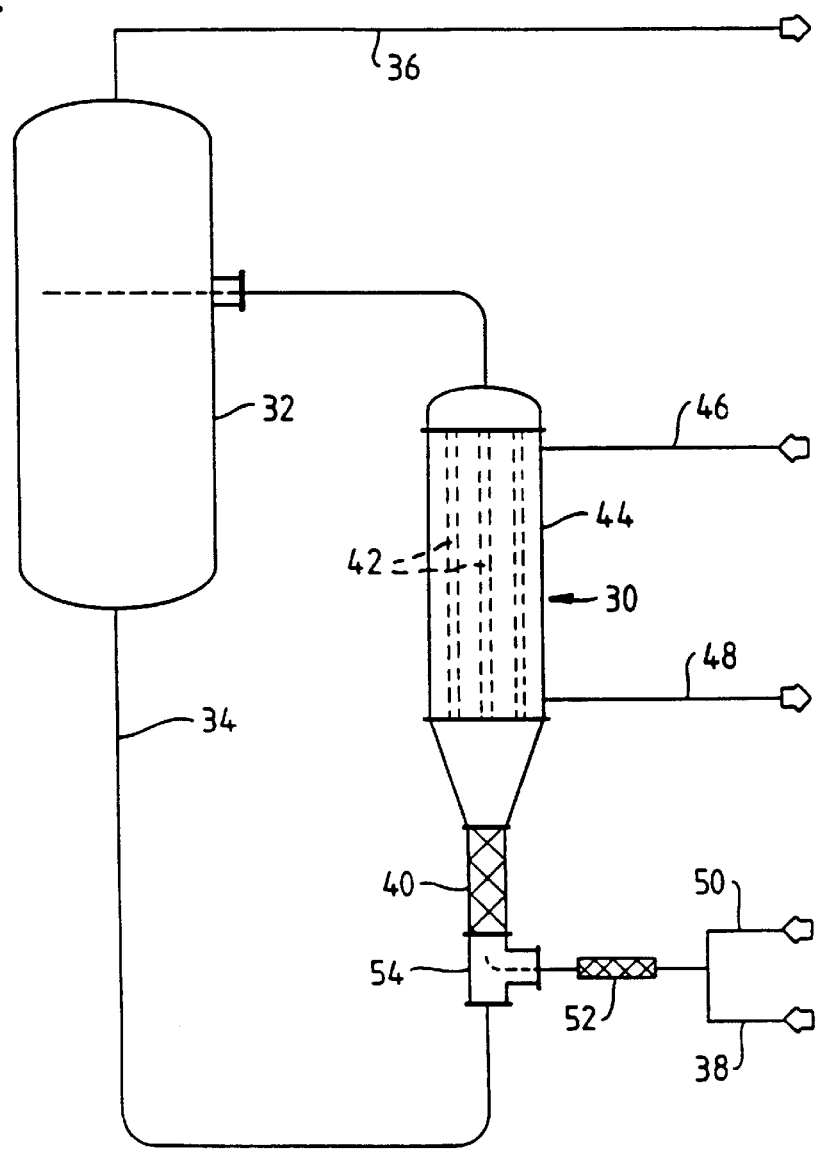
FIG. 2 is a schematic view of apparatus for effecting vaporisation of trichloro-ethylene.

Referring to FIG. 2, the apparatus for effecting vaporisation of trichloroethylene comprises an thermosiphon boiler 30 and a disengagement vessel 32 connected to receive boiling liquid/vapour from the boiler 30. Within the vessel 32, the liquid and vapour phases are disengaged, the liquid phase being returned to the base of the boiler 30 via line 34 and the vapour phase being supplied to the reactor system via line 36. The liquid recirculation is induced by virtue of the density difference between the separated liquid in the falling leg and the boiling liquid/vapour mixture rising through the boiler 30. The recycled liquid phase is combined with fresh trichloroethylene supplied via line 38, mixed within static mixer section 40 and subjected to further heating by passage through vertical tubes 42 which pass through jacket 44. A suitable heating medium, such as steam condensing at a suitable temperature, is circulated through the jacket 44 via lines 46, 48.

If trichloroethylene is vaporised at high pressure, such that the boiling temperature is in excess of 150° C. or even high (eg in excess of 180° C.), degradation products are formed which cause fouling of the heat exchange surfaces of the boiler 30. The rate of formation of these degradation products increases as the vaporisation temperature increases. The problem of vaporising trichloroethylene without the production of significant quantities of degradation products is achieved by effecting the vaporisation of the compound in admixture with anhydrous hydrogen fluoride. The presence of HF has been found to be effective in lowering the temperature at which vaporisation of trichloroethylene can be effected (eg at pressures in excess of 6 bara) which means that, where the trichloroethylene has to be vaporised at pressure conditions normally requiring it to be heated to temperatures at which it tends to degrade, the presence of HF permits vaporisation to be effected at lower temperatures without significant generation of degradation products. In addition, it is suspected that the mere presence of HF also tends to inhibit the breakdown of trichloroethylene into degradation products.

Thus, HF is also supplied to the boiler via line 50 and is intimately pre-mixed with the incoming trichloroethylene by means of static mixer 52. The resulting mixture is then combined with the liquid phase returning from the disengagement vessel 32 in mixing T-piece 54 and the combined flows are subjected to mixing in static mixer section 40 before coming into heat exchange relation with the heating fluid employed by the boiler 30. Typically, the rate of recirculation (mass per unit time) of the liquid phase mixture from the disengagement vessel 32 to the boiler is of the order of 5 to 10 times the rate of vaporisation. The bottom section of the boiler 30 is of conical configuration to facilitate smooth entry of the liquid into the boiler.

It will be understood that the presence of HF allows the temperature at which the boiler operates to be reduced. It is important that the trichloroethylene and HF components are thoroughly mixed since, during co-vaporisation of the mixed components, the liquid composition becomes rich in trichloroethylene compared with the vapour phase; consequently any imperfections in mixing of the components may lead some parts of the feedstream to become so depleted in HF that vaporisation of trichloroethylene at the lower temperature of operation ceases.

Figure 3:
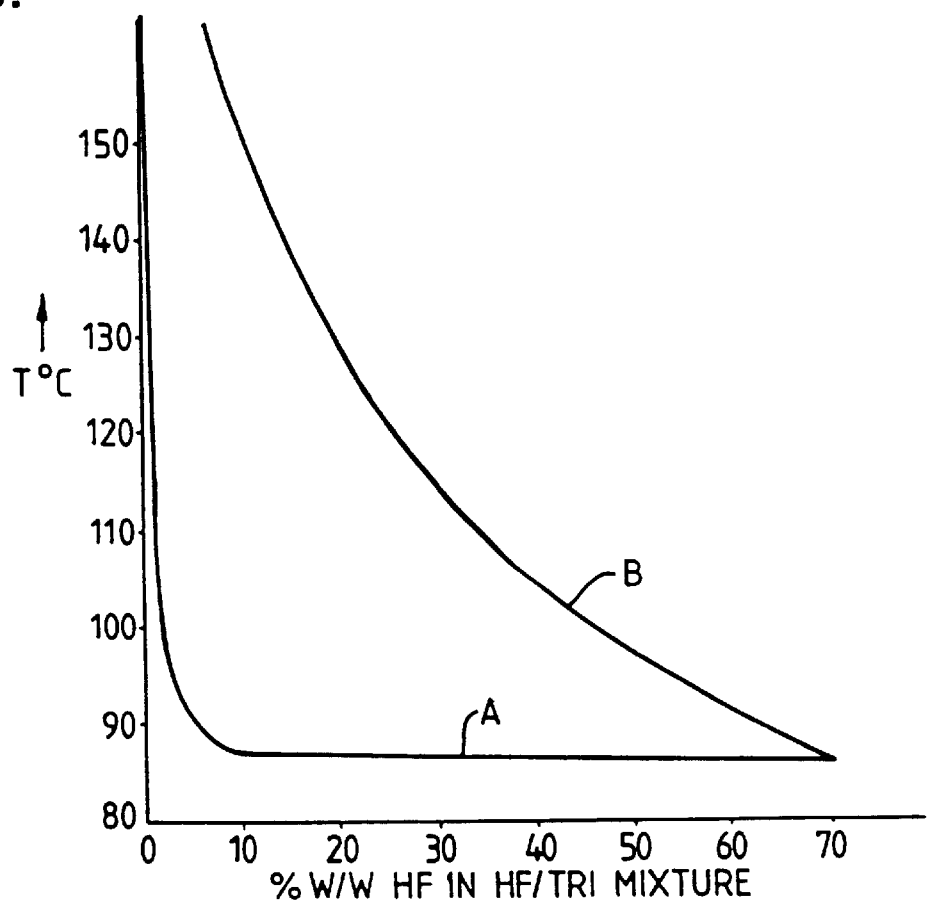
FIG. 3 is a liquid/vapour equilibrium diagram for trichloroethylene and hydrogen fluoride.

The amount of anhydrous HF employed in the co-vaporisation process may vary widely since the suppression effect has been observed to be very marked even when the proportion of HF present in the liquid phase trichloroethylene/HF mixture is less than 1% by weight, eg as low as 0.1% by weight. The effect of introducing HF into the trichloroethylene is illustrated in FIG. 3 which shows the trichloroethylene/HF liquid/vapour equilibrium for the pressure of 8.6 bara. Curves A and B represent the liquid and vapour phases respectively. In the complete absence of HF, the boiling point of trichloroethylene is 181.3° C. However, even small additions of HF (less than 1% by weight) can be seen to have a marked affect on the boiling point. For instance, at a temperature of 140° C., a substantial amount of trichloroethylene is present in the vapour phase; vaporisation of the trichloroethylene at this temperature significantly suppresses the formation of degradation products. In addition to substantially eliminating the risk of degradation, the resulting reduction in vaporisation temperature secured by addition of HF gives a cooler vapour for introduction into the line 14 which assists cooling of the process stream from reactor 10 thereby reducing the cooling duty demanded of the cooler in line 14.

During steady state operation, the amounts of trichloroethylene and HF introduced via lines 38 and 50 are selected to correspond to the point on the vapour phase curve B corresponding to the temperature at which it is desired to effect vaporisation of the liquid phase mixture of trichloroethylene and HF.

The vapour obtained from the disengagement vessel is utilised in the fluorination process described in relation to FIG. 1. The presence of HF in this vapour is of course acceptable since it forms one of the reactants used in the fluorination process and the HF introduced by this route may constitute a means of supplementing HF supply into the process since the co-vaporisation process may be carried out even where the HF forms a substantial or even major part of the liquid phase mixture. Usually however in the process of FIG. 1, substantial amount of HF will already be present in the process stream passing from the reactor 12 to the reactor 10 and it is not necessary to supplement the process with additional HF at this point in the process. Consequently the amount of HF employed in the co-vaporisation with trichloroethylene may be minimal, less than 1% by weight in the liquid trichloroethylene/HF mixture.

The particular heat exchange apparatus shown in FIG. 2 for effecting the co-vaporisation is only one of a number of suitable designs that may be employed. Other designs will be readily apparent to those skilled in the art; for instance, instead of a separate disengagement vessel as shown in FIG. 2, the disengagement vessel may form an integral part of the thermo-siphon reboiler. Or instead of a thermo-siphon reboiler, co-vaporisation may be carried out in an kettle-type boiler. Whatever form the heat exchange apparatus takes, it will be understood that efficient mixing of the boiling components in the liquid phase is important and that the apparatus therefore needs to be designed in such a way as to secure good mixing. The necessary design expedients required to achieve this are well known to those skilled in the art. For instance, in the case of a kettle drum apparatus using a tube-in-shell design with steam as the heating medium on the tube side, we have found that good mixing can be achieved by introducing the liquid phase mixture into the shell via a plurality of nozzles at different locations along the length of the apparatus and employing a pumped recirculation loop for recirculating the unvaporised trichloroethylene rich liquid phase (following disengagement from the vapour) into the trichloroethylene/HF feed. Typically the pumped recirculation rate (mass per unit time) is of the order of 5 to 10 times the vaporisation rate.

Although the invention is described above with reference to the vaporisation of trichloroethylene, the technique described above is applicable to the co-vaporisation of other compounds prone to degradation with another compound or compounds capable of producing a substantial increase in the volatility of the first-mentioned compound; particularly suitable combinations of compounds are those which form minimum boiling azeotropes having a liquid-vapour equilibrium diagram generally similar to that of the trichloroethylene/HF mixture (FIG. 3). One such combination is 1,1,2,2-tetrachloroethane and HF.

Figure 4:
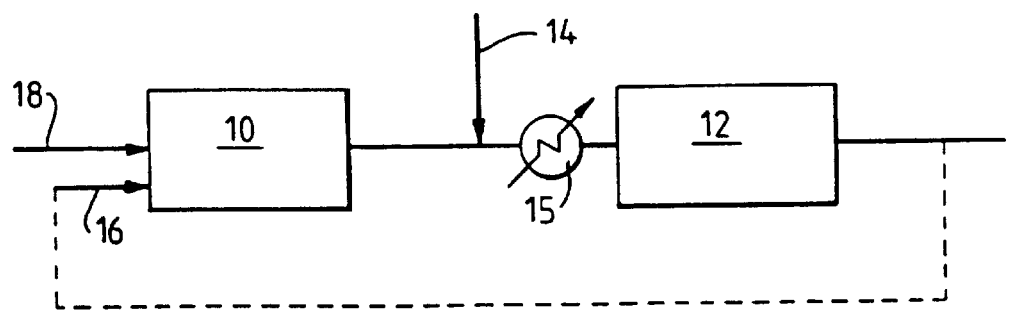
FIG. 4 is a schematic view similar to that of FIG. 1.

Referring now to the process illustrated in FIG. 4, this process is generally the same as that described with reference to FIG. 1 and like components are depicted using the same reference numbering but preceded with the prefix "1". The reactors 110, 112 are interconnected by a conduit 114. The reaction carried out in reactor 112 is effected at a lower temperature than that carried out in reactor 110 and hence some cooling, by cooler 115, is required prior to introduction of the reactants into reactor 112. In addition, by mixing relatively cool trichloroethylene vapour with the hot gaseous stream (typically at a temperature of the order of 330° C.) from reactor 10, the cooling power input required of the cooler 116 may be reduced. In this aspect of the present invention, instead of vaporising the trichloroethylene prior to mixing it with the hot gaseous product stream from the reactor 110, the trichloroethylene is is added to the hot gaseous stream passing through conduit 114 by injecting liquid phase trichloroethylene at a temperature of the order of at least 100° C., typically 100 to 150° C., into the conduit 114. In this way, the trichloroethylene is atomised into droplets by, and thereafter vaporised by, the hot gaseous stream and the relatively colder liquid trichloroethylene assists in cooling the hot gaseous stream prior to entry into the reactor 112. It is preferred to preheat the liquid trichloroethylene prior to introduction into the process gas stream in order to reduce its viscosity and surface tension and thereby aid atomisation, while lowering its density and hence increasing the velocity of the injected stream for a given mass flow rate.

Figure 5:
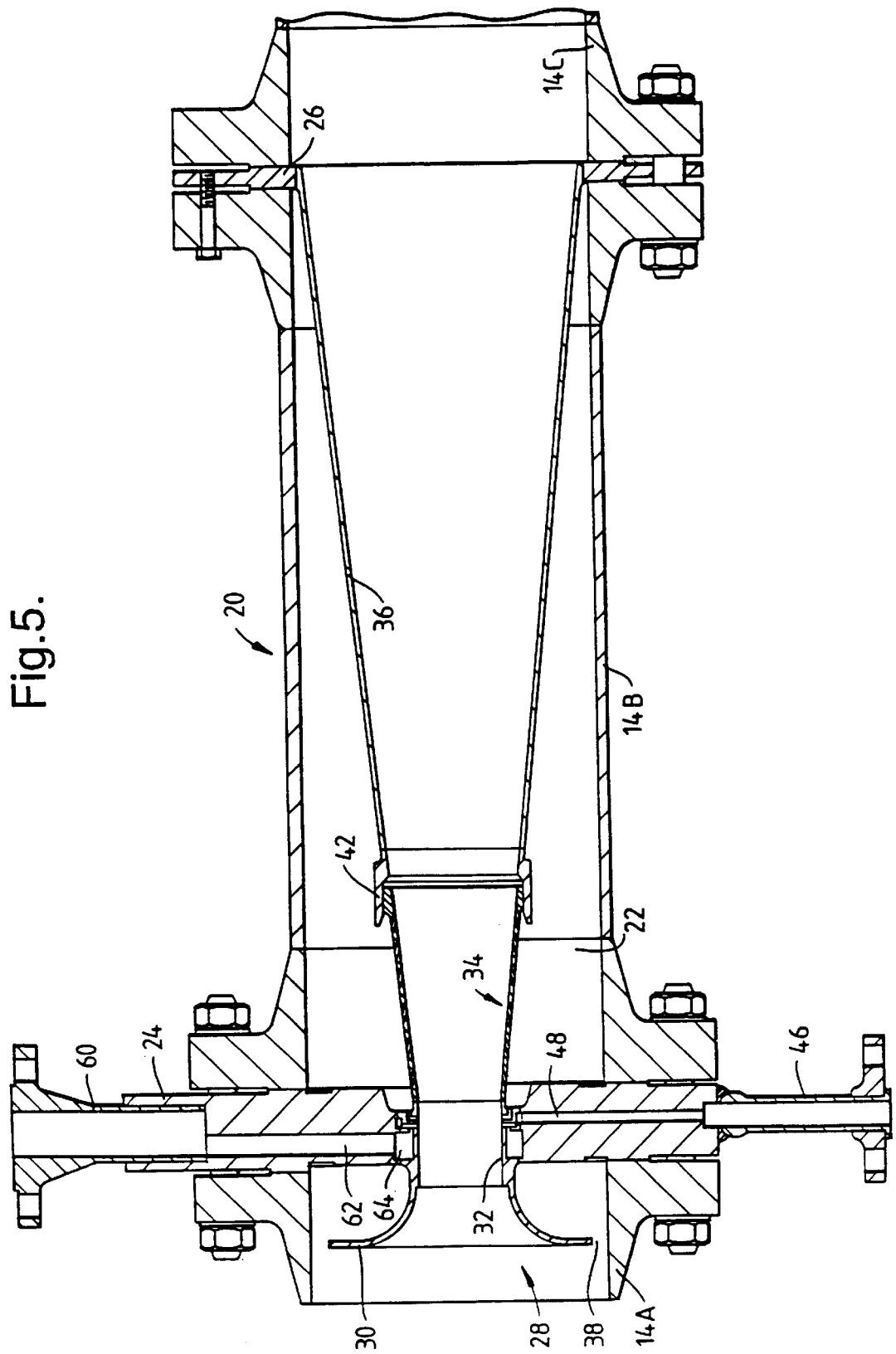
FIG. 5 is a schematic view in longitudinal section of part of the conduit extending between the reactors in which the two-stage process of FIG. 4 is carried out, showing one form of liquid spraying arrangement for introducing liquid phase trichloroethylene into the hot gaseous stream passing between the reactors.

Referring to FIG. 5, the conduit 114 incorporates a vaporising unit 120 in which spraying and vaporisation of the liquid trichloroethylene is effected. If liquid trichloroethylene is simply injected into the conduit 114, there is a substantial risk of degradation occurring since the conduit surfaces are at a relatively high temperature and, unless substantially complete vaporisation of the trichloroethylene is achieved, liquid trichloroethylene can settle onto such surfaces and undergo degradation.

Figure 6:
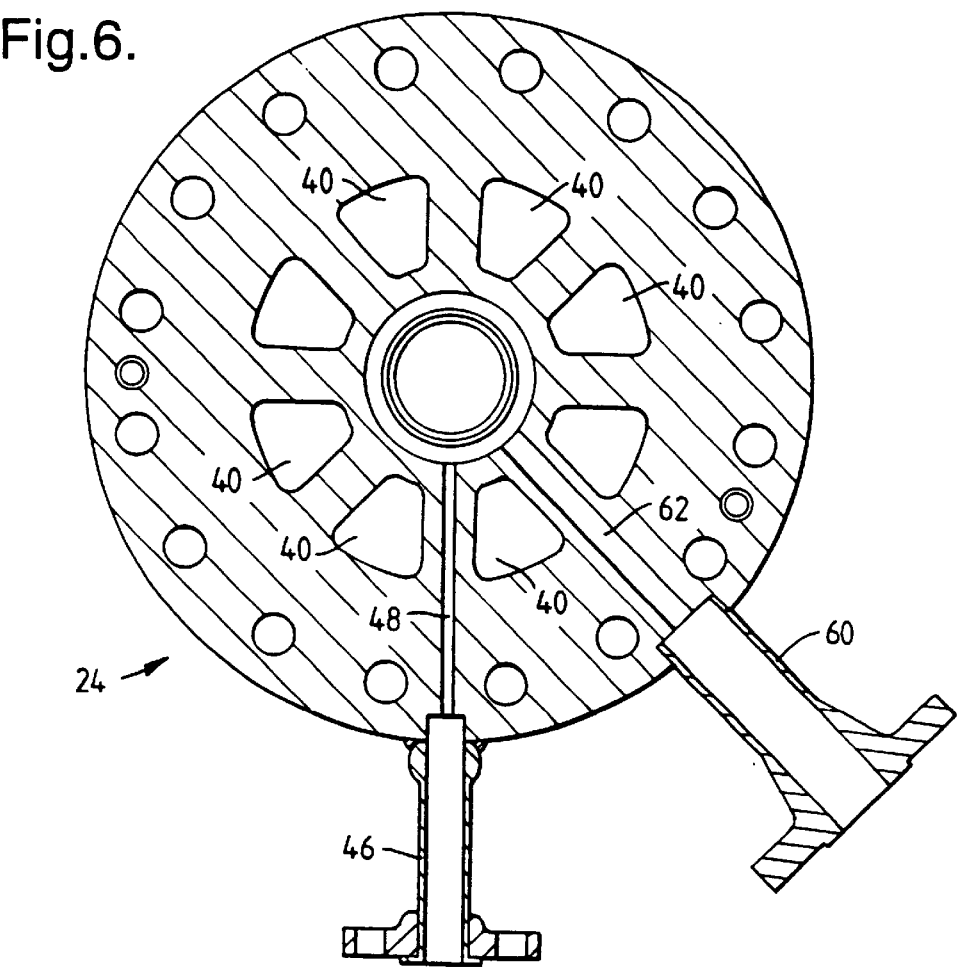
FIG. 6 is a diagrammatic view in transverse section of the vaporising unit shown in FIG. 5.

The vaporising unit 120 comprises a Venturi arrangement 122 located by annular housing 124 and support flange 126 clamped between successive conduit sections 114A, B and C within the conduit section 114A. The Venturi arrangement 22 comprises an upstream section 128 defining an outwardly flared portion 130 leading to the Venturi throat 132, an intermediate section 134 and a downstream section 136, sections 134 and 136 being of progressively increasing cross-section in the direction of process gas flow. The upstream section 128 has an outer diameter which is less than the internal diameter of the upstream conduit section 114A so that part of the process gas is diverted from the main flow through annular gap 138 and externally of the upstream section 128. The remaining process gas passes through the Venturi throat 132 and undergoes a pressure drop and accompanying increase in velocity. The annular housing 124 is formed with a number of openings 140 (see FIG. 6) through which the process gas can flow and enter the conduit section 114B externally of the sections 134 and 136.

The sections 134 and 136 are coupled by joint 142 so as to provide a smooth transition between the two sections. Section 134 is located immediately upstream of the Venturi throat 132 and it is in this region that there may be a tendency for droplets of liquid phase trichloroethylene to settle and degrade if allowed to reside on the hot metal. To overcome this, a layer of process gas is developed over the surface of the section 134. This is achieved by forming a multiplicity of axially and circumferentially distributed holes 144 (eg laser drilled holes) in the wall of the section 134 so that the diverted gas flow is allowed to re-enter the Venturi arrangement at this location. The holes 144 may be arranged as an array having a triangular pitch and are oriented with their axes extending obliquely so as assist formation of a boundary-like layer of gas over the internal surface of the section 134. In this manner, any liquid droplets tending to settle on the internal surface of the section 134 are swept away and back into the main flow. In the illustrated embodiment, the holes 144 are confined to the section 134; however, it will be appreciated that in some cases it may be necessary to extend the array of holes further along the conduit section 114B. Any residual gas diverted from the main flow rejoins the main flow via openings 145 located in the vicinity of flange 126.

Figure 7:
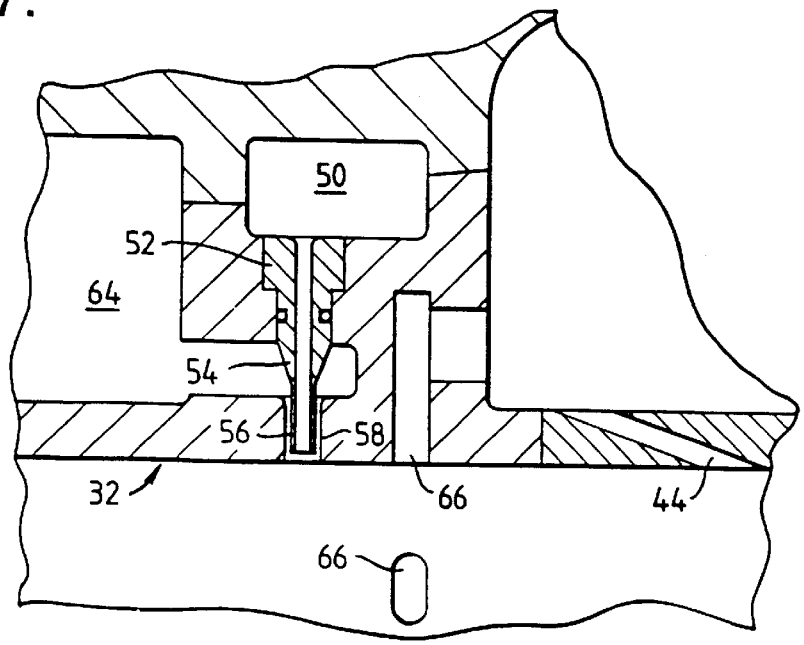
FIG. 7 is an enlarged view showing the injector nozzles.
Figure 1:
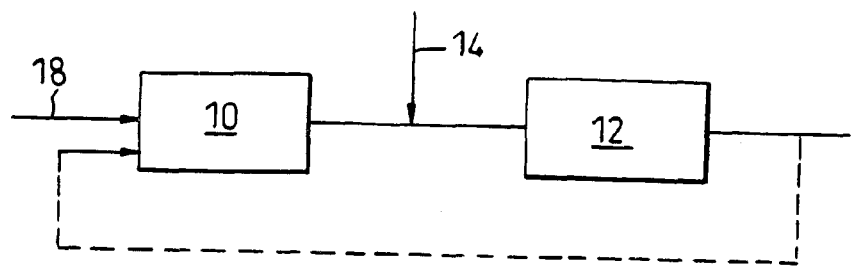
Figure 2:
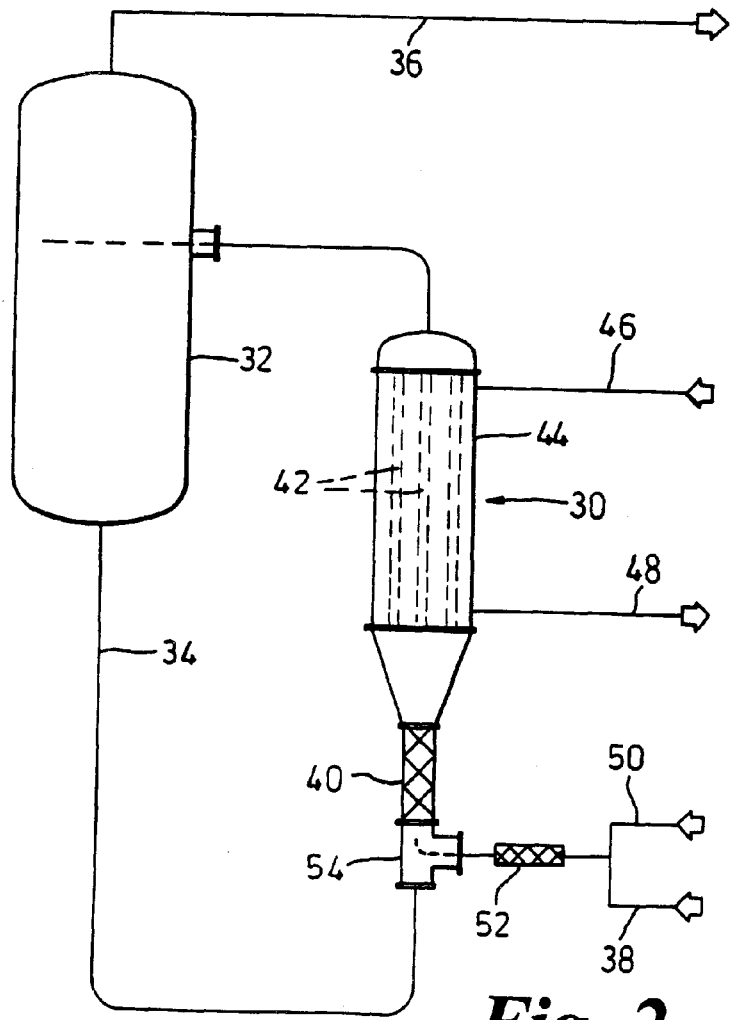
Figure 3:
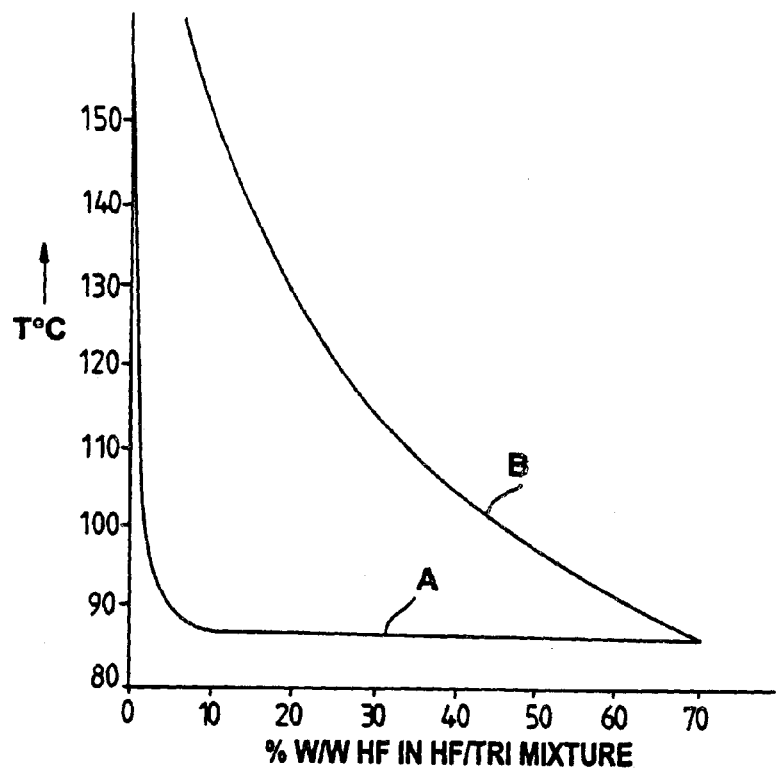
Figure 4:
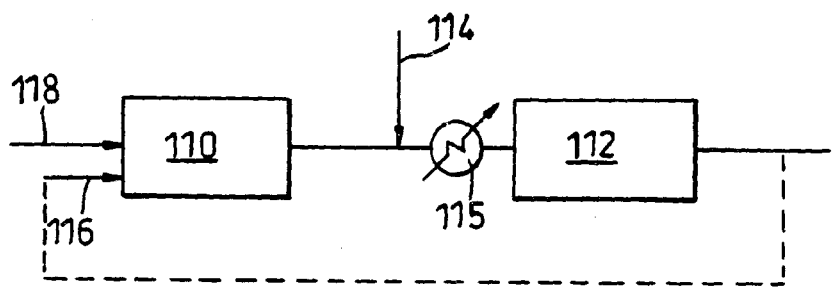
Figure 6:
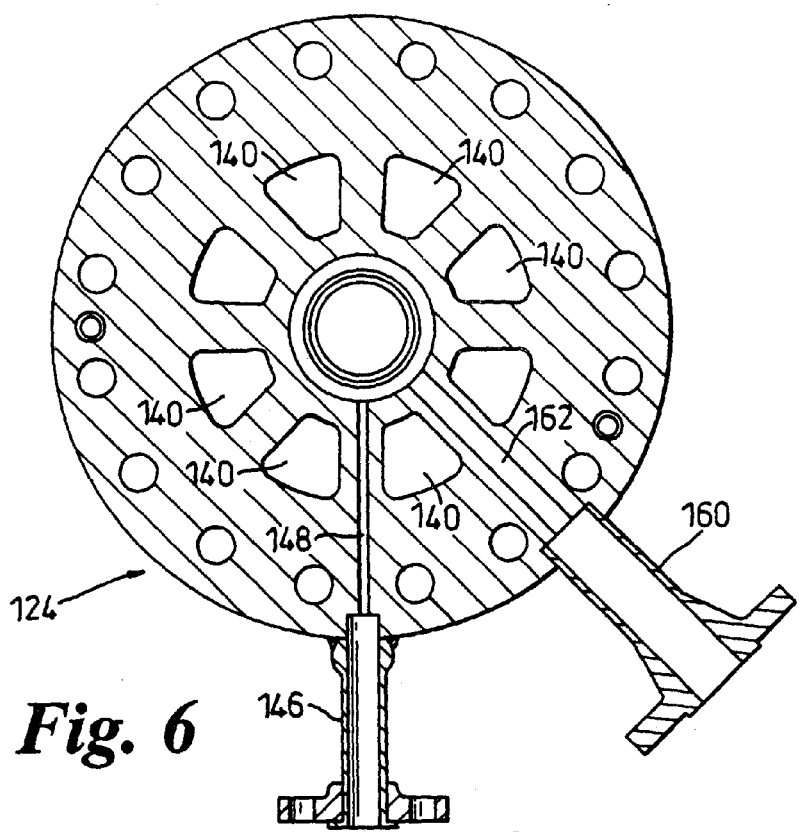
Figure 7:
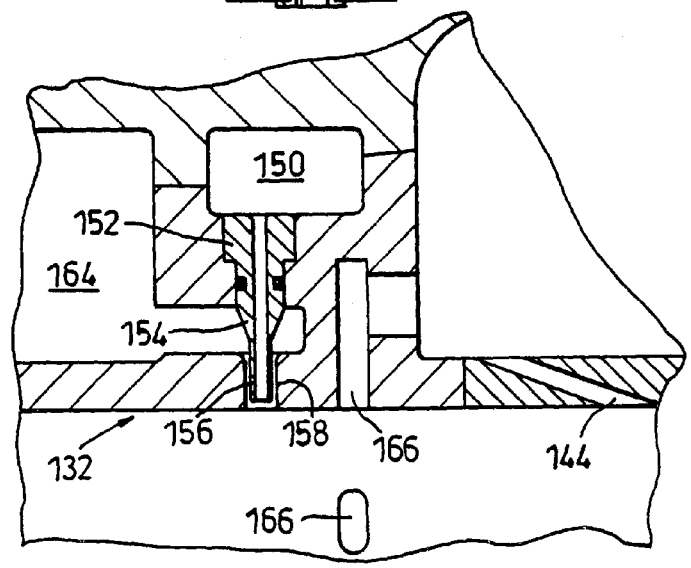

The liquid phase component to be introduced into the conduit 114 is supplied under pressure via inlet 146 (see FIGS. 5 and 6) connected to the housing 124 in registry with radial passage 148 leading to an annular gallery 150 (see FIG. 7). The gallery 150 feeds a set of equiangularly spaced nozzles 152 each of the form shown in FIG. 7. The number of liquid supply nozzles 152 will depend on the particular process conditions; typically there may be of the order of 20, spaced at equal intervals so that the liquid supplied from gallery 150 is distributed substantially uniformly between nozzles 152. Each nozzle 152 comprises a body 154 which is secured (for example by brazing) within a respective bore in the annular housing 124 and has a conical section 154 leading to a narrow open ended cylindrical section 156 through which the liquid is discharged. The section 156 extends with clearance through passage 158 which opens into the Venturi throat 132. The section 156 terminates at a location radially outwardly of the inner periphery of the throat 132 so that liquid discharged from section 156 has to traverse a small gap within the confines of passage 158 before it enters the Venturi throat 132.

For reasons that will become apparent later, the liquid injection via the nozzles 152 is accompanied at each nozzle location by injection of gas (conveniently HF in the case of a process involving the fluorination of trichloroethylene). The gas is introduced by inlet 160 connected to the housing 124 in registry with passageway 162 leading to an annular gallery 164 coaxial with the throat section 132. Gas entering the gallery 164 is distributed substantially uniformly between the passages 158 associated with the nozzles 152 and passes into the throat section via the annular clearance gaps between the nozzle bodies and the passages 158. In this manner, the gas and liquid enter the throat section 132 in co-current fashion. The gas introduced in this manner is conveniently preheated to lower its density thereby increasing its exit velocity for a given mass flow and allowing the dimensions of the nozzle and annular passages to be maximised and hence less sensitive to blockage by debris. Gas exit velocity is of importance with respect to the efficiency of atomisation which is governed by the "shear action" between the liquid and gas.

In addition to discharging gas into the throat section 132 via passages 158, gas is also discharged into the throat section 132 through a series of equiangularly spaced outlets 166 each located immediately downstream and in axial alignment with a respective nozzle 152. The gas supply to these nozzles may be derived from the gas supplied via inlet 160 or it may be derived independently; for instance in the illustrated embodiment it is bled from the process gas diverted around the Venturi arrangement via gap 138 and is forced through the orifices 166 by the pressure differential created between the main bulk gas flow and the reduced pressure existing at the Venturi throat.

Atomisation of the liquid is achieved by one or both of two mechanisms depending on the process operating conditions. When the process is operating under low load conditions with the process gas throughput turned down, atomisation is primarily attributable to the shear effect of the co-current flow liquid discharging through the nozzles 152 and the gas discharging through the clearance gaps around the nozzles. As the load increases and the process gas throughput flowing through the conduit 114 increases, the "cross-flow" shear affect, ie flow of gas normal to the direction of liquid injection, becomes a significant mechanism for the atomisation process. Thus, the droplet size and dispersion regime of the liquid is predominantly governed initially by the co-current shear affect and as the load increases it is governed mainly by the "cross-flow" shear affect. The use of shear-type mechanisms for producing atomisation allows the physical space requirements of a system using pressure injection to be substantially reduced.

In practice, it is convenient to inject gas via the passages 158 continuously since changes in the operating conditions can be catered for without intervention be an operator. Thus, if the load conditions are undergoing reduction, any loss in atomisation efficiency as a result of the reduced process gas flow rate through conduit 114 (and hence less effective "cross-flow" atomisation) may be compensated for automatically by the co-current atomisation obtained from the gas introduced via passages 158.

The number, arrangement and dimensional relationships of the nozzles will generally depend on the process operating conditions. In practice, the nozzles will usually be designed so as to produce droplets of a suitable median size and size distribution for the process in question, consistent with the need to ensure vaporisation by means of the enthalpy available from intimate mixing with the process gas (and the gas supplied via passages 158). As the gas supplied via passages 158 may also play a role in the vaporisation of the liquid droplets, especially in process turn-down conditions, the gas is as mentioned previously preheated to a temperature consistent with this role. The extent of preheating may be made dependent on the process load conditions.

Other factors governing the design and arrangement of the nozzles include injection in such a way as to reduce the tendency for the droplets to migrate towards the walls of sections 134 and 136 and also to prevent injection of droplets beyond the central axis of the throat 132 and sections 134, 136 which could otherwise lead to increased propensity for droplet coalescence and increased tendency to migrate towards the walls. The position of the nozzles 152, particularly the radially inner ends thereof, relative to the internal surface of the Venturi throat 132 has been found to be important in terms of achieving good atomisation and preventing re-entrainment of the injected liquid phase component on to the internal surfaces of the Venturi arrangement. Suitable positioning of the nozzles can be determined empirically for given conditions by means of flow visualisation models. Similarly, for given conditions, the number and extent of holes 144 formed downstream of the point of liquid injection may be determined empirically.

By way of example, in a typical arrangement involving a pipe section of 250 mm diameter, the Venturi throat may have a diameter of 70 mm and there may be 20 nozzles 152 spaced equiangularly around the Venturi throat 132, each nozzle being arranged with its inner extremity spaced radially outwardly of the surface of the Venturi throat by a distance of the order of 0.5 mm. The cross-sectional area of the nozzle outlets is typically of the order of 0.65 mm$^2$ and the cross-sectional area of the annular passages 158 in the immediate proximity of the nozzle outlets is typically of the order 2.5 mm$^2$. The holes 144 in a typical arrangement are distributed on a triangular pitch configuration as a series of circumferential rows, eg 12 rows, each comprising for instance 60 obliquely oriented holes having a diameter of 1.27 mm.

In operation of the vaporisation unit, the droplets formed are entrained in the process gas and are caused to vaporise without coming into contact with the hot walls of the conduit or the Venturi arrangement. Any droplets (such as droplets having sizes at the extremes of the size distribution) tending to migrate towards the walls are swept away from contact by the moving boundary layer of gas secured by bleeding process gas through the holes 144. The amount of process gas employed for this purpose will in general depend on the particular process conditions; typically a minor fraction (eg 20%) of the process gas will be diverted for this purpose. The gas flow introduced by means of the outlets 166 serves to overcome any tendency of the liquid to deposit on the walls immediately downstream of the nozzles. At these locations, a localised pressure drop exists in the wake of each jet of liquid which, in the absence of gas injected via outlets 166, could result in the liquid depositing on the hot wall surfaces of the Venturi throat 132.

In a typical application, the process gas stream is at an elevated pressure (usually above 6 bara, eg 13 bara) and a temperature in excess of 300° C. The liquid injected via nozzles 152 is typically at a much lower temperature (eg 100° C.) as is the gas introduced via passages 158 which will usually be at a temperature higher than the liquid (eg 150° C.). The liquid and gas are introduced at a pressure in excess of the process gas stream, eg a differential pressure of 9 bar and 2 bar respectively.

Although the invention is described above in relation to FIGS. 4 to 7 with reference to a process for the production of 134a, the invention is also applicable to other processes requiring injection of a liquid phase component into a hot gaseous stream in circumstances where the liquid phase component is prone to degrade as a result coming into contact with a hot metal surface.

What is claimed is:

1. A process for carrying out a chemical reaction which comprises vapourising a first organic compound which comprises a halocarbon which has been vapourised from the liquid state under conditions which render the liquid phase form of the pure compound prone to degrade wherein vapourisation of said first organic compound from the liquid phase is effected using a second compound which is capable of forming an azeotropic mixture with said first organic compound in such a way that degradation of said first compound is suppressed.

2. A process as claimed in claim 1 in which the chemical reaction comprises reaction of said first compound with another compound.

3. A process as claimed in claim 2 in which the other compound comprises said second compound.

4. A process as claimed in claim 3 in which said second compound is used in its liquid phase.

5. A process as claimed in claim 1 in which the chemical reaction comprises isomerisation of the first compound.

6. A process as claimed in any one of claims 1 to 5 in which vaporisation of the first compound is effected by co-vaporisation thereof with the second compound.

7. A process for carrying out a chemical reaction at elevated pressure comprising vapourising under elevated pressure conditions a liquid phase organic compound which comprises a halocarbon and which is prone to degrade when vapourised under such conditions, and reacting the vapourised compound with at least one other reactant in the vapour phase under conditions which permit the reaction to proceed by modifying the boiling characteristics of the organic compound such that vapourisation can be effected at reduced temperature thereby preventing or substantially reducing the production of degradation products wherein vapourisation of said organic compound from the liquid phase is effected using a second compound which is capable of forming an azeotropic mixture with said organic compound.

8. A process as claimed in claims 1 or 7 in which the halocarbon comprises a chloroethene or chloroethane.

9. A process as claimed in claim 7 in which the boiling characteristics of the organic compound are modified by co-vaporising the compound in admixture with another compound forming one of the reactants.

10. A process as claimed in claim 7 in which said organic compound is one which provides a mixture capable of forming a minimum boiling azeotrope with the other reactant.

11. A process for carrying out a chemical reaction which process comprises utilizing a halocarbon in its vapour phase, in which prior to the reaction the halocarbon is vapourised under elevated pressure conditions at which the boiling point of the compound is such that vapourisation of the compound is accompanied by degradation of the compound if vapourised at that boiling point wherein the halocarbon is co-vapourised in admixture with hydrogen fluoride whereby the boiling temperature of the halocarbon compound/hydrogen fluoride mixture is such that vapourisation is accompanied by substantially less degradation of the halocarbon compound.

12. A process for effecting fluorination of a chlorocarbon compound at elevated pressure comprising vapourising the compound under elevated pressure conditions at which the boiling point of the compound is such that vapourisation of the compound is accompanied by degradation of the compound if vapourised at that boiling point and reacting the vapourised compound with hydrogen fluoride in the gaseous phase under conditions which permit the reaction to proceed, and effecting vapourisation of the chlorocarbon by co-vapourising a mixture of the chlorocarbon compound with hydrogen fluoride whereby the boiling temperature of the chlorocarbon compound/hydrogen fluoride mixture is such that vapourisation is accompanied by substantially less degradation of the chlorocarbon compound.

13. A process as claimed in claim 11 or 12 in which chlorocarbon compound is a chloroethene or a chloroethane.

* * * * *

UNITED STATES PATENT AND TRADEMARK OFFICE
CERTIFICATE OF CORRECTION

PATENT NO.    : 6,288,292 B1
DATED         : September 11, 2001
INVENTOR(S)   : Scott et al.

It is certified that error appears in the above-identified patent and that said Letters Patent is hereby corrected as shown below:

<u>Drawings,</u>
Delete Sheets 1, 2, 3 and 4 containing FIGS. 1-7 and substitute sheets 1, 2, 3 and 4 of drawings containing FIGS. 1-7 as shown on the attached sheets 1, 2, 3 and 4.

<u>Column 8,</u>
Line 31, "10" should be -- 110 --.
Line 62, "22" should be -- 122 --.

<u>Column 10,</u>
Line 40, "be" should be -- by --.

Signed and Sealed this

Twentieth Day of May, 2003

JAMES E. ROGAN
*Director of the United States Patent and Trademark Office*

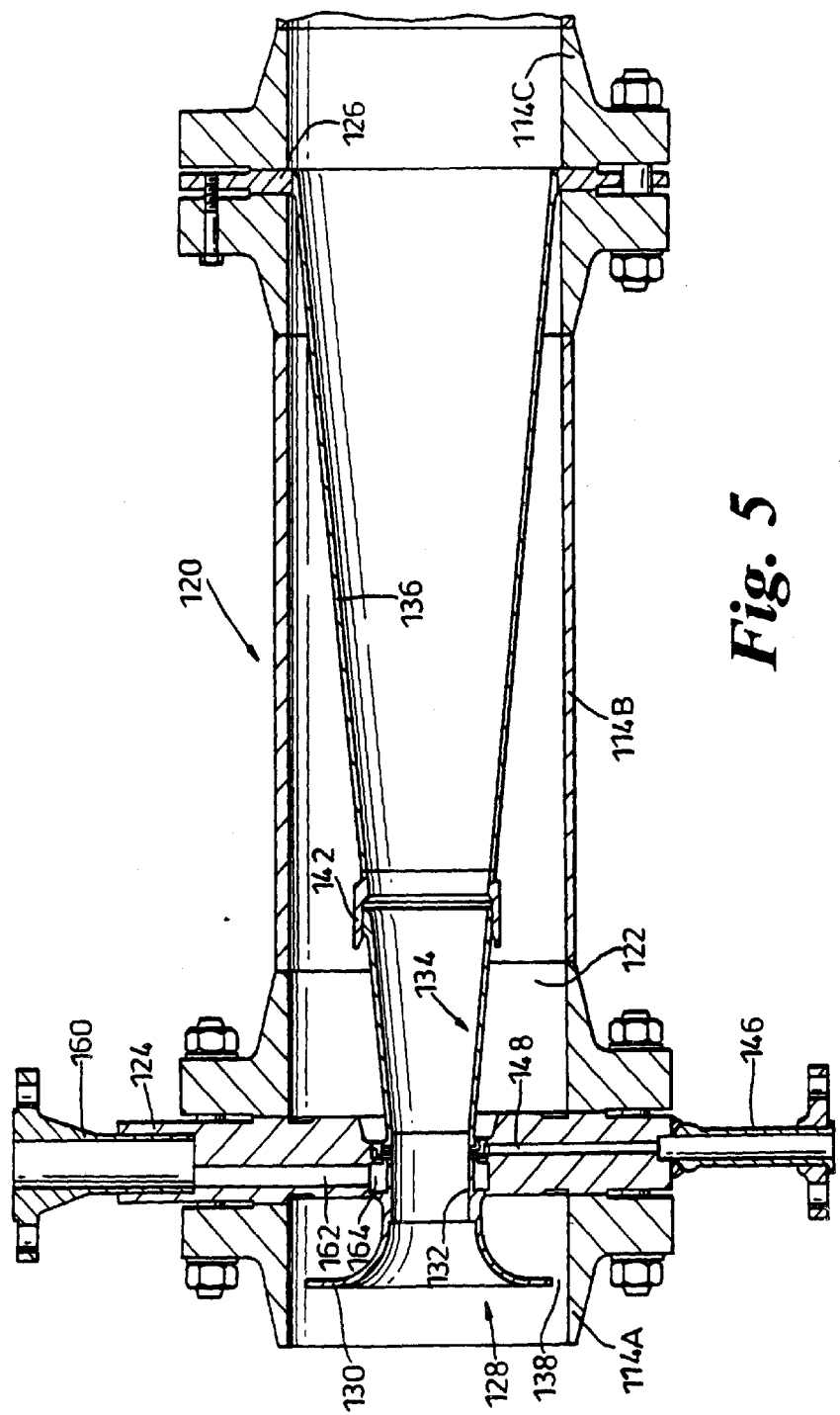

UNITED STATES PATENT AND TRADEMARK OFFICE
CERTIFICATE OF CORRECTION

PATENT NO.    : 6,288,292 B1
DATED         : September 11, 2001
INVENTOR(S)   : Scott et al.

It is certified that error appears in the above-identified patent and that said Letters Patent is hereby corrected as shown below:

Title page,
Between items [63] and [51], insert the following:

-- [30]  Foreign Application Priority Data
Apr. 22, 1993   [GB]   United Kingdom ............. 9308373
Apr. 22, 1993   [GB]   United Kingdom ............. 9308374 --

Signed and Sealed this

Fifteenth Day of July, 2003

JAMES E. ROGAN
*Director of the United States Patent and Trademark Office*